United States Patent
Yamada

(10) Patent No.: US 9,669,047 B2
(45) Date of Patent: Jun. 6, 2017

(54) METHOD FOR PRODUCING POLYPHENOL COMPOSITION

(71) Applicant: KAO CORPORATION, Tokyo (JP)

(72) Inventor: Yasushi Yamada, Narita (JP)

(73) Assignee: KAO CORPORATION, Tokyo (JP)

( * ) Notice: Subject to any disclaimer, the term of this patent is extended or adjusted under 35 U.S.C. 154(b) by 53 days.

(21) Appl. No.: 14/758,111

(22) PCT Filed: Dec. 26, 2013

(86) PCT No.: PCT/JP2013/084797
§ 371 (c)(1),
(2) Date: Jun. 26, 2015

(87) PCT Pub. No.: WO2014/104157
PCT Pub. Date: Jul. 3, 2014

(65) Prior Publication Data
US 2015/0335673 A1 Nov. 26, 2015

(30) Foreign Application Priority Data
Dec. 27, 2012 (JP) ................................ 2012-284338

(51) Int. Cl.
| | | |
|---|---|---|
| *A61K 31/192* | (2006.01) | |
| *A61K 31/216* | (2006.01) | |
| *A61K 31/353* | (2006.01) | |
| *A61K 31/36* | (2006.01) | |
| *A61K 31/366* | (2006.01) | |
| *A61K 31/7048* | (2006.01) | |
| *C07D 311/32* | (2006.01) | |
| *A23L 33/10* | (2016.01) | |

(52) U.S. Cl.
CPC .......... *A61K 31/7048* (2013.01); *A23L 33/10* (2016.08); *A61K 31/192* (2013.01); *A61K 31/216* (2013.01); *A61K 31/353* (2013.01); *A61K 31/36* (2013.01); *A61K 31/366* (2013.01); *C07D 311/32* (2013.01)

(58) Field of Classification Search
None
See application file for complete search history.

(56) References Cited

U.S. PATENT DOCUMENTS

| | | |
|---|---|---|
| 5,456,923 A | 10/1995 | Nakamichi et al. |
| 2004/0013736 A1 | 1/2004 | Nakano et al. |
| 2006/0153936 A1 | 7/2006 | Tsuzaki |
| 2011/0189311 A1 | 8/2011 | Tozuka et al. |
| 2013/0085270 A1 | 4/2013 | Yamada et al. |

FOREIGN PATENT DOCUMENTS

| | | | |
|---|---|---|---|
| JP | 2007-161588 A | 6/2007 | |
| JP | 2007-208414 A | 8/2007 | |
| JP | 2007-308414 A | 11/2007 | |
| JP | 2008-271839 A | 11/2008 | |
| JP | 2011-51938 A | 3/2011 | |
| JP | 2012-17322 A | 1/2012 | |
| WO | WO 92/18106 A1 | 10/1992 | |
| WO | WO 2005/003112 A1 | 1/2005 | |
| WO | WO 2011/155505 A1 | 12/2011 | |
| WO | WO 2012049253 A1 * | 4/2012 | ............. A61K 9/145 |

OTHER PUBLICATIONS

International Search Report issued in PCT/JP2013/084797, mailed on Mar. 11, 2014.
Maeda et al., "Removal of Hesperidin in Satsuma Mandarin (*Citrus unshiu* Marc.) Juice with Adsorbents", Nihon Shokuhin Kogyo Gakkaishi, 1985, vol. 32, No. 5, pp. 344-348.
English translation of the International Preliminary Report on Patentability and Written Opinion of the International Searching Authority (Forms PCT/IB/338, PCT/IB/373 and PCT/ISA/237), dated Jul. 9, 2015, for International Application No. PCT/JP2013/084797.

* cited by examiner

*Primary Examiner* — Layla Berry
(74) *Attorney, Agent, or Firm* — Birch, Stewart, Kolasch & Birch, LLP

(57) ABSTRACT

Provided is a method for easily producing a polyphenol composition in a solid state having an excellent solubility in water. The method for producing the polyphenol composition comprises the following steps (1) and (2): (1) heating a mixture of a hardly water-soluble polyphenol (A) and a water-soluble polyphenol (B) to a temperature equal to or higher than the lowest melting point or glass transition temperature of the hardly water-soluble polyphenol (A) or the water-soluble polyphenol (B), thereby obtaining a heat-treated solution, and (2) cooling and solidifying the thus-obtained heat-treated solution.

17 Claims, 1 Drawing Sheet

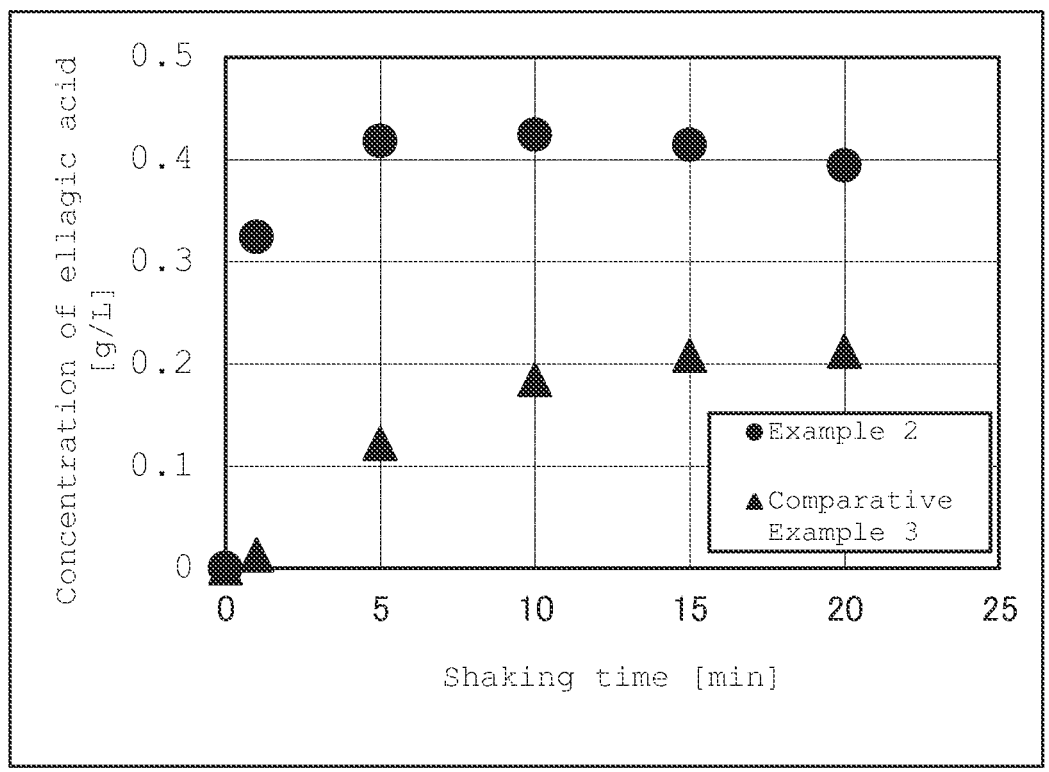

METHOD FOR PRODUCING POLYPHENOL COMPOSITION

FIELD OF THE INVENTION

The present invention relates to a method for producing a polyphenol composition.

BACKGROUND OF THE INVENTION

Recently, various materials having a physiological function have been proposed, and many health foods containing these materials are available in the market. Among them, polyphenols are known to have an antioxidative activity and are considered as an important component of the health foods because of their expected effects such as antiarteriosclerotic effect, antiallergic effect and augmentation effect of blood stream.

However, since many polyphenols are hardly soluble in water, it is difficult to use them for foods and drinks, and the like.

The technique for solubilizing a hardly water-soluble polyphenols into water has been investigated. For example, it is reported that a method for solubilizing hesperidin by subjecting hesperidin and hesperidin-sugar adduct to a heat treatment at 100 to 180° C. in the presence of an aqueous medium (Patent Document 1).

CITATION LIST

Patent Document

[Patent Document 1] JP-A 2012-17322
[Patent Document 2] JP-A 2011-51938
[Patent Document 3] WO-A 1992/18106 pamphlet.

SUMMARY OF THE INVENTION

The present invention provides a method for producing a polyphenol composition comprising the following steps (1) and (2): (1) heating a mixture of a hardly water-soluble polyphenol (A) and a water-soluble polyphenol (B) to a temperature equal to or higher than the lowest melting point or glass transition temperature of the hardly water-soluble polyphenol (A) or the water-soluble polyphenol (B), thereby obtaining a heat-treated solution, and (2) cooling and solidifying the thus-obtained heat-treated solution.

DETAILED DESCRIPTION OF THE INVENTION

The technique disclosed in the Patent Document 1 relates to the acceleration of solubilization of hardly water-soluble polyphenols. A complication of the process would be concerned because the step for removing a solvent such as water is required in order to convert the polyphenols into the solid state for easy handling, and the like.

On the other hand, as a technique for improving the solubility, absorbability, and the like of hardly water-soluble medicaments, a method for mixing an ethanol solution of a hardly water-soluble medicament in ethanol with an aqueous solution of a water-soluble compound such as an enzyme-treated hesperidin, and spraying and drying the resulting mixed solution is known (Patent Document 2). Also, known is a method for producing a solid dispersion of a medicament dispersed on a polymer support by heating, melting and blending the medicament and the polymer support followed by cooling and pulverizing (Patent Document 3). The method of the Patent Document 2 also requires the removal of the solvent.

The technique disclosed in the Patent Document 3 has a problem that a high shear force is needed at heating and melting since the melt has a high viscosity, which requires a high cost and significant labor.

In view of these problems, the present invention provides a method for easily producing a polyphenol composition in a solid state having an excellent solubility in water.

As a result of the intensive study on the above-mentioned problems, the present inventor found that the polyphenol composition in a solid state having an excellent solubility in water is obtained by mixing a hardly water-soluble polyphenol and a water-soluble polyphenol and heating the mixture to a temperature equal to or higher than the lowest melting point or glass transition temperature of the hardly water-soluble polyphenol or the water-soluble polyphenol, followed by cooling after liquefying, thereby remarkably increasing a concentration of the dissolved hardly-soluble polyphenol in water.

According to the present invention, the concentration of the dissolved hardly water-soluble polyphenol in water can be increased, and a polyphenol composition in a solid state having the excellent water solubility can be easily produced.

BRIEF DESCRIPTION OF THE DRAWINGS

FIG. 1 shows the initial solubility of an ellagic acid composition in water at 25° C.

DETAILED DESCRIPTION OF THE INVENTION

The step (1) of the present invention is a step for heating a mixture of a hardly water-soluble polyphenol (A) and a water-soluble polyphenol (B) to a temperature equal to or higher than the lowest melting point or glass transition temperature of the hardly water-soluble polyphenol (A) or the water-soluble polyphenol (B) thereby obtaining a heat-treated solution.

The term "hardly water-soluble polyphenol" used in the present invention refers to the one having a poor solubility in water. The solubility at 25° C. of such polyphenol is, for example, 2 g/L or less, preferably 1 g/L or less, more preferably 0.5 g/L or less, more preferably 0.2 g/L or less, even more preferably 0.05 g/L or less. The solubility represents herein a gram number of the solute being dissolved in 1 L of the solution with a unit of [g/L].

As the hardly water-soluble polyphenol (A), a phenolic compound having one or more, preferably two or more hydroxyl groups bonded to a benzene ring may be preferably used. The example thereof includes plant-derived flavonoid, tannin, phenolic acid, and the like. As more preferred hardly water-soluble polyphenols, flavonols, flavanones, flavones, isoflavones, phenol carboxylic acids, anthocyanidins, hydroxycinnamic acid derivatives, ellagic acid, lignan, and the like are exemplified.

Specific examples include flavonols such as rutin, quercitrin, isoquercitrin, quercetin, myricitrin, myricetin, kaempferol; flavanones such as hesperidin, neohesperidin, hesperetin, naringin; flavones such as ringenin, prunin, astragalin, apiin, apigenin; isoflavones such as daidzein, daidzin, glycitein, glycitin, genistein, genistin; curcumins such as curcumin; anthocyanidins such as delphinidin, delphin, nose peonidin, peonin, petunin, malvidin, malvin, enin, cyanidin, leukocyanidin, cyanine, chrysanthemine, keracyanin, idaein, mecocyanin, pelargonidin, callistephin; hydroxy cinnamic acid derivatives such as resveratrol, caffeic acid, ferulic acid, p-coumaric acid; ellagic acid; lignans such as sesamin, sesaminol, sesamolin sesamol, and the like. Among them, flavanones, hydroxy cinnamic acid derivatives, ellagic acid and ligan are preferable, hesperidin, ferulic acid, ellagic acid and sesamin being more preferable. The hardly water-soluble polyphenols may be used solely or as a mixture of two or more kinds.

The hardly water-soluble polyphenols (A) of the present invention include not only aglycone but also glycosides having aglycone bonded to a sugar, as long as they fulfill the above-mentioned definition.

The examples include hesperidin, which is a glycoside of hesperetin (5,7,3'-trihydroxy-4'-methoxyflavanone) having rutinose (L-rhamnosyl-($\alpha$1→6)-D-glucose) β-bonded to the hydroxyl group at its 7th position, apiin, which is a glycoside of apigenin having apiose and glucose bonded thereto, rutin, which is a glycoside of quercetin having rutinose bonded thereto, quercitrin, which is a glycoside of quercetin having rhamnose bonded thereto, and the like.

The water-soluble polyphenol (3) used in the present invention is a polyphenol having higher solubility in water than that of the hardly water-soluble polyphenol (A) to be used together. Specifically, it is preferable that the solubility of the water-soluble polyphenol (B) in water at 25° C. is 2 times or higher, more preferably 5 times or higher, even more preferably 10 times or higher than that of the hardly water-soluble polyphenol (A) in water at 25° C. More specifically, the solubility in water at 25° C. is 10 g/L or more, preferably 15 g/L or more, more preferably 20 g/L or more.

Examples of such water-soluble polyphenol (B) include sugar adducts of hardly water-soluble polyphenols, methylated products of hardly water-soluble polyphenols, catechins, chlorogenic acids, and the like, among which glucosylhesperidin, methylhesperidin, catechins, and chlorogenic acids are preferable. They may be used solely or in a combination of two or more kinds.

The sugar adduct of the hardly water-soluble polyphenol used in the present invention is a compound composed of the above-mentioned hardly water-soluble polyphenol having at least one sugar bonded thereto. The type of the sugar to be bonded to the hardly water-soluble polyphenol is not particularly limited, and at least one selected from the group consisting of tetrose, pentose and hexose, such as glucose, galactose, fructose, rhamnose, xylose, arabinose, erythrose is preferable. The number of the sugar to be bonded is preferably from 1 to 10, more preferably from 1 to 6. The bonding position of the sugar to the hardly water-soluble polyphenol is the phenolic hydroxyl group or the sugar residue of the glycoside. The bonding mode of the hardly water-soluble polyphenol and the sugar may be α-bonding or β-bonding.

The sugar adduct of the hardly water-soluble polyphenol is preferably glucosylhesperidin, glucosylrutin, glucosylquercetin, and glucosylisoquercitrin. Among them, glucosylhesperidin and glucosylrutin are more preferable.

The sugar adduct of the hardly water-soluble polyphenol may be industrially produced by known method utilizing the chemical synthesis or enzymatic reaction.

Commercially available preparations, such as "Hayashibara Hesperidin S" (Hayashibara Biochemical Laboratories, Inc.) and "Glucosylrutin B" (Toyo Seita Co., Ltd.) may be also used as the sugar adduct of the hardly water-soluble polyphenol.

The methylated product of the hardly water-soluble polyphenol used in the present invention is obtained by methylation of the above-mentioned hardly water-soluble polyphenol followed by solubilizing in water. The position and the number of the methylation are not particularly limited. Specifically, methylhesperidin, methylquercetin, methylresveratrol, methylrutin and the like are exemplified, among which methylhesperidin is preferable. It is known that methylhesperidin mainly includes chalcone-type compound (1) and flavanone-type compound (2). As its structural component, the following structures are exemplified.

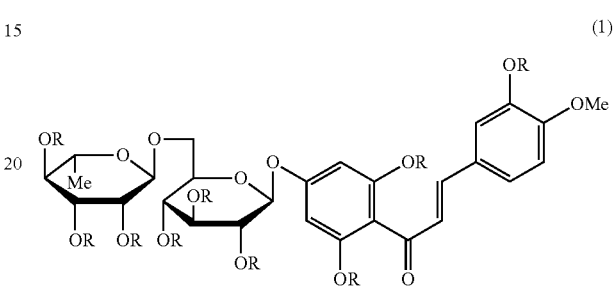

(1)

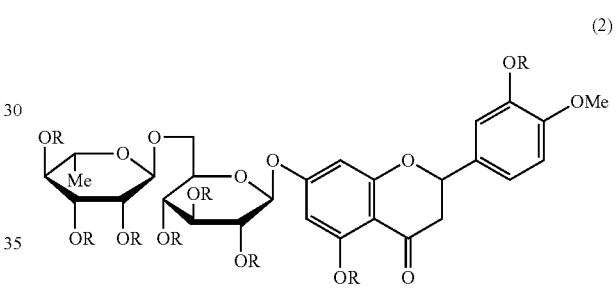

(2)

wherein R represents a hydrogen atom or a methyl group.

It is noted that methylhesperidin as a pharmaceutical additive and a food additive is mainly used as a mixture of the compound (3) and compound (4).

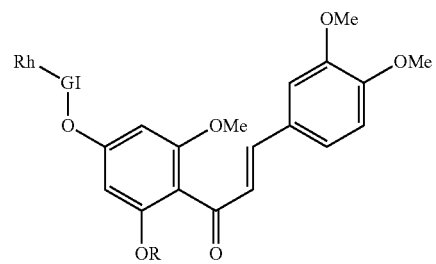

(3)

|       | R  | Gl-2 | Rh-2 |
|-------|----|------|------|
| (3-1) | Me | Me$_2$ | H    |
| (3-2) | H  | Me   | H    |
| (3-3) | H  | H    | H    |

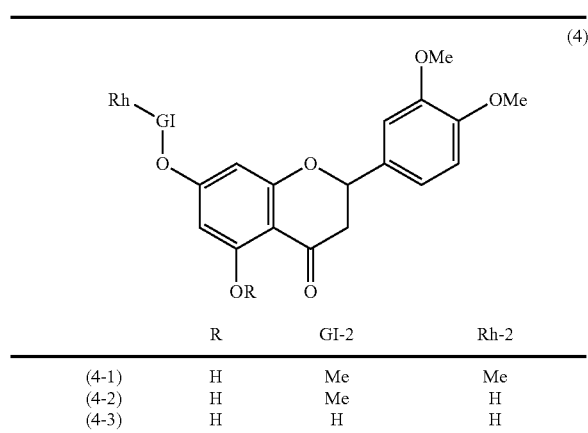

(4)

| | R | Gl-2 | Rh-2 |
|---|---|---|---|
| (4-1) | H | Me | Me |
| (4-2) | H | Me | H |
| (4-3) | H | H | H | wherein Gl and Rh represent a glucose residue and a rhamnose residue, respectively. Gl-2 and Rh-2 represent 2-position of the glucose residue (In the case of 3-1, 3-position is also included), and 2-position of the rhamnose residue, respectively.

Hesperidin methylchalcone as a raw material for cosmetics is used as a compound represented by (5). It is noted that the composition which contains a large amount of chalcone type compound is also referred to as hesperidin methylchalcone.

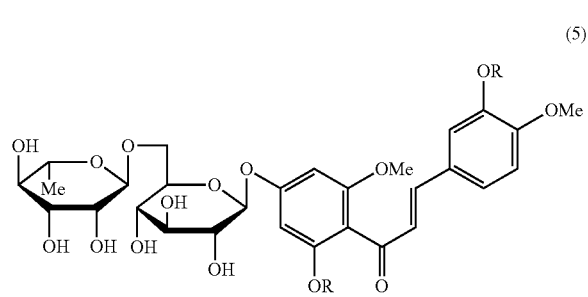

(5)

wherein R represents a hydrogen atom or a methyl group.

Methylhesperidin used in the present invention may contain both of the chalcone-type compound (1) and the flavanone-type compound (2) mentioned above, or may contain either of them.

A more preferred methylhesperidin in the present invention is a mixture of the compound (3) and the compound (4).

Methylhesperidin may be produced in accordance with a known method, for example, by dissolving hesperidin in an aqueous solution of sodium hydroxide, allowing the alkaline solution thereof to react with a corresponding amount of dimethyl sulfate, neutralizing the reaction solution with sulfuric acid, extracting the resulting mixture with n-butyl alcohol, and evaporating the solvent therefrom, followed by recrystallization using isopropyl alcohol (Sakieki, Nippon Kagaku Zassi, 79, 733-6 (1958)). The production method is not limited to this one.

A commercially available methylhesperidin-containing preparation may be used as methylhesperidin, and for example, includes "Methyl hesperidin" (Tokyo Chemical Industry Co., Ltd.), "Hesperidin methylchalcone" (Sigma. Co.) and "Methylhesperidin" (Hamari Chemicals Ltd.).

The catechins used in the present invention is a generic term, which encompasses non-epi-form catechins such as catechin, gallocatechin, catechin gallate and gallocatechin gallate, and epi-form catechins such as epicatechin, epigallocatechin, epicatechin gallate and epigallocatechin gallate. The content of the catechins is defined based on the total amount of 8 types mentioned above.

As the catechins, a tea extract may be used. As the tea extract, at least one selected from the group consisting of tea extract solution, the concentrate thereof and the purified product thereof may be used.

The "tea extract solution" herein means the extract solution from tea leaves with hot water or a water-soluble organic solvent, without being subjected a concentration or purification operation. As the water-soluble organic solvent, for example, lower alcohols such as ethanol may be used. As the extraction method, known methods such as kneader extraction, stirring extraction (batch extraction) countercurrent extraction (drip extraction), column extraction and the like may be used.

Tea leaves used for extraction may be roughly classified into a non-fermented tea, a semi-fermented tea and a fermented tea, depending on the processing method. As the non-fermented tea, green tea such as sencha, bancha, gyokuro, tencha, kamairicha, kukicha, boucha, mecha, is exemplified. As the semi-fermented tea, oolong tea such as tekkannon, irotane, ougonkei, buigancha is exemplified. Further, as fermented tea, black teas such as Darjeeling, Assam and Ceylon is exemplified. These teas may be used either solely or in a combination of two or more. Of these, green tea is preferable from the standpoint of the content of the catechins.

The term "concentrate of tea extract solution" means one obtained, from a solution which has been extracted from tea leaves selected from the group consisting of non-fermented tea, semi-fermented tea and fermented tea with hot water or a water-soluble organic solvent, with the catechins at a concentration raised by removing a part of water, and can be prepared, for example, by the method disclosed in JP-A-59-219384, JP-A-4-20589, JP-A-5-260907, JP-A-5-306279 and the like. The form thereof includes solid, aqueous solution, slurry and the like. Commercially available products of the concentrated tea extract solution may be used. For example, the concentrated green tea extract solution such as "POLYPHENON" (product of Mitsui Nor in Co., Ltd.), "TEAFURAN" (product of ITO EN, LTD.), "SUNPHENON" (product of Taiyo Kagaku Co., Ltd.) is exemplified.

A purification of the tea extract solution and the like may be carried out using a solvent and a column.

Chlorogenic acids used in the present invention is a generic term, which collectively encompasses monocaffeoylguinic acids including 3-caffeoylquinic acid, 4-caffeoylquinic acid and 5-caffeoylquinic acid, monoferuloylquinic acids including 3-feruloylquinic acid, 4-feruloylquinic acid and 5-feruloylquinic acid, and dicaffeoylquinic acids including 3,4-dicaffeoylquinic acid, 3,5-dicaffeoylquinic acid and 4,5-dicaffeoylquinic acid. The content of chlorogenic acids is defined based on the total amount of 9 types mentioned above.

In addition, chlorogenic acids may be in the form of a salt. The example as the salt includes a salt with an alkaline metal such as sodium, potassium, a salt with an alkaline earth metal such as magnesium, calcium, a salt with an organic amine such as monoethanolamine, diethanolamine, triethanolamine, and a salt with a basic amino acid such as arginine, lysine, histidine, ornithine, and the like.

As chlorogenic acids, the plant extract containing this, the concentrate thereof, the purified product thereof and the like may be used. As such plant extract, for example, extract from sunflower seed, unripe apple fruit, green coffee bean, simon leaves, strobile of pine family plant, seed husk of pine family plant, leaves of sugar cane nandina, burdock, peel of eggplant, fruit of Japanese plum, colts foot, vitaceae family plant and the like is exemplified. Among them, green coffee bean extract is preferable in view of a content of chlorogenic acids and the like. As for the kind of coffee tree, any of coffee Arabica, Coffee Robusta, Coffee Liberica and Coffee Arabusta may be used. Methods and conditions for extraction, concentration and purification are not particularly limited, and known methods and conditions may be used.

As the chlorogenic acids, commercially available chlorogenic acid-containing preparation such as, for example, Flavor Holder RC (T. Hasegawa Co., Ltd.) may also be used.

In the present invention, a mass ratio of the hardly water-soluble polyphenol (A) to the water-soluble polyphenol (B) when these polyphenols are mixed, [(A)/(B)], is preferably 0.05 or more, more preferably 0.09 or more, more preferably 0.1 or more, more preferably 0.11 or more, more preferably 0.13 or more, even more preferably 0.15 or more, in view of increasing the content of the hardly water-soluble polyphenol (A) in the resulting polyphenol composition and in view of the cost of the resulting polyphenol composition. The mass ratio [(A)/(B)] is preferably 2 or less, more preferably 1 or less, more preferably 0.5 or less, more preferably 0.4 or less, even more preferably 0.25 or less, in view of the water solubility of the resulting polyphenol composition. The ratio [(A)/(B)] is preferably from 0.05 to 2, more preferably from 0.09 to 1, more preferably from 0.1 to 0.5, more preferably from 0.11 to 0.4, even more preferably from 0.13 to 0.25. Note that the mass of the hardly water-soluble polyphenol (A) in the present invention is expressed in terms of the anhydrous substance if it is a hydrate.

The mixture of the hardly water-soluble polyphenol (A) and the water-soluble polyphenol (B) may contain sugar or sugar alcohol as a plasticizer.

Examples of the preferred plasticizer include glucose, fructose, maltose, mannose, rhamnose, ribose, xylose, trehalose, xylytol, sorbitol, mannitol and erythritol.

A content of the aqueous medium in the mixture of the hardly water-soluble polyphenol (A) and the water-soluble polyphenol (B) at the heat treatment is preferably 10 mass % or less, more preferably 5 mass % or less, more preferably 2 mass % or less, more preferably 1 mass % or less, even more preferably the mixture substantially does not contain the aqueous medium.

Note that the amount of the aqueous medium does not include the hydrated water contained in the hardly water-soluble polyphenol (A) or the water-soluble polyphenol (B).

The aqueous medium in the present invention is water and an aqueous solution of an organic solvent. Tap water, distilled water, ion exchanged water, and purified water are exemplified as the water. The organic solvent is not particularly limited, as long as it is miscible with water homogeneously. Alcohols having 4 or less carbon atoms is exemplified as the organic solvent, and propanol and ethanol are exemplified.

The method of the heat treatment of the mixture of the hardly water-soluble polyphenol (A) and the water-soluble polyphenol (B) is not particularly limited, and a known method may be used. It is preferable that the mixture is heated while stirring. For example, an extruder or a kneading machine such as a kneader may be used. A stirring machine such as a ribbon mixer may be also used.

The heat treatment is performed at a temperature equal to or higher than the lowest melting point or glass transition temperature of the hardly water-soluble polyphenol (A) or the water-soluble polyphenol (B). The mixture of the hardly water-soluble polyphenol (A) and the water-soluble polyphenol (B) is molten by heating at such temperature. Polyphenols are compatible each other because they have many similar functional groups in their structure. Therefore, by heating to melt or soften either one of the hardly water-soluble polyphenol (A) or the water-soluble polyphenol (B), another polyphenol dissolves therein.

In addition, it is more preferable that the mixture is heated to a temperature equal to or higher than the lowest melting point or glass transition temperature of the water-soluble polyphenol (B), because the water-soluble polyphenol (B) significantly involves the solubilization of the hardly water-soluble polyphenol (A).

A temperature for the heat treatment is higher than the lowest melting point or glass transition temperature of the hardly water-soluble polyphenol (A) or the water-soluble polyphenol (B) preferably by 2° C. or higher, more preferably by 5° C. or more, even more preferably by 10° C. or more, in view of reducing the viscosity of the mixture and achieving a homogeneous mixing. The temperature of the heat treatment is higher than the lowest melting point or glass transition temperature of the water-soluble polyphenol (B) preferably by 2° C. or more, more preferably by 5° C. or more, even more preferably by 10° C. or more.

For example, in the case of methylhesperidin having the melting point of 135° C., the temperature for the heat treatment is preferably 135° C. or higher, more preferably 137° C. or higher, more preferably 140° C. or higher, more preferably 150° C. or higher, even more preferably 160° C. or higher.

In the case of glucosylhesperidin having the glass transition temperature of 150° C., the temperature is preferably 150° C. or higher, more preferably 152° C. or higher, more preferably 155° C. or higher, even more preferably 160° C. or higher.

In the case of chlorogenic acid having the glass transition temperature of 140° C., the temperature is preferably 140° C. or higher, more preferably 142° C. or higher, more preferably 145° C. or higher, more preferably 150° C. or higher, even more preferably 160° C. or higher.

In the case of epigallocatechin gallate (melting point 147° C.), which belongs to catechins, the temperature is preferably 147° C. or higher, more preferably 149° C. or higher, more preferably 152° C. or higher, more preferably 157° C. or higher, even more preferably 160° C. or higher.

The melting point or glass transition temperature of the hardly water-soluble polyphenol (A) and the water-soluble polyphenol (B) may be measured by differential scanning calorimetry.

The temperature for the heat treatment is preferably 200° C. or lower, more preferably 180° C. or lower, in view of the heat stability of the polyphenols.

The temperature for the heat treatment is preferably higher than the lowest melting point or glass transition temperature of the hardly water-soluble polyphenol (A) or the water-soluble polyphenol (B) by 2° C. or more and up to 180° C., more preferably higher than the lowest melting point or glass transition temperature of the hardly water-soluble polyphenol (A) or the water-soluble polyphenol (B) by 5° C. or more, and up to 180° C., even more preferably higher than the lowest melting point or glass transition temperature of the hardly water-soluble polyphenol (A) or the water-soluble polyphenol (B) by 10° C. or more, and up to 180° C. Heating means include, for example, steam and electricity.

A time for the heat treatment is preferably from 0.1 to 30 minutes, more preferably from 0.2 to 15 minutes, even more preferably from 0.5 to 10 minutes after the temperature has reached the lowest melting point or glass transition temperature of the hardly water-soluble polyphenol (A) or the water-soluble polyphenol (B), in view of enhancement of solubility and heat stability of the hardly water-soluble polyphenol.

The step (2) is a step for cooling and solidifying the heat-treated solution obtained in step (1).

The cooling temperature for the heat-treated solution is preferably lower than the melting point or glass transition temperature of the polyphenol having the lowest melting point or glass transition temperature of the hardly water-soluble polyphenol (A) and the water-soluble polyphenol (B), and is preferably 100° C. or lower, more preferably 60° C. or lower, in view of prevention of crystallization of the hardly water-soluble polyphenol (A).

The cooling method is preferably placing the heat-treated solution under an atmosphere at 40° C. or lower, or more preferably at room temperature (23° C.). It is preferable that the mixture after the heat treatment is quenched by blowing cold air thereto.

The cooling rate of the heat-treated solution, which is calculated from the time required to lower the temperature from the heat treatment temperature down to 25° C., is preferably 0.2° C./s or more, more preferably 0.5° C./s or more, more preferably 1.0° C./s or more, even more preferably 3.0° C./s or more, and, for example, 100° C./s or less, more preferably 50° C./s or less, in view of the limitation of the manufacturing equipment.

In the present invention, it is preferable to perform a step for pulverizing the cooled and solidified polyphenol composition, in view of shaping into products with various forms. Pulverization may be performed using a pulverizing machine such as a cutter-type pulverizer including a grinder and a roll cutter, an impact-type pulverizer including a hammer mill, a grinding-type pulverizer including a colloid mill, and the like. The pulverizing conditions such as the pulverizing time and the revolution of the pulverizer may be determined as needed.

The polyphenol composition thus-obtained is in a solid state and has an excellent solubility in water. Thus, the solubility of the hardly water-soluble polyphenol (A) in water at 25° C. in the polyphenol composition obtained is increased, preferably 3 times or more, more preferably 5 times or more, more preferably 9 times or more, even more preferably 10 times or more.

An initial solubility of the hardly water-soluble polyphenol (A) in water at 25° C. in the polyphenol composition of the present invention is preferably from 0.1 to 1000 g/L, more preferably from 0.2 to 100 g/L. The term "initial" herein means a time period from dissolution to water to 20 minutes.

The polyphenol composition obtained according to the production method of the present invention may be used for various foods and drinks and pharmaceuticals, and the like. Among others, the aqueous solution in which the polyphenol composition is dissolved is useful as a beverage due to a low viscosity and a feeling as the be passes down through the throat. Examples of the beverage include tea, sport drink, isotonic drink, near water, and the like.

The present invention further discloses the following producing method and the composition in regard to the above-mentioned embodiment.

<1> A method for producing a polyphenol composition comprising the following steps (1) and (2):
(1) heating a mixture of a hardly water-soluble polyphenol (A) and a water-soluble polyphenol (B) to a temperature equal to or higher than the lowest melting point or glass transition temperature of the hardly water-soluble polyphenol (A) or the water-soluble polyphenol (B), thereby obtaining a heat-treated solution, and (2) cooling and solidifying the thus-obtained heat-treated solution.

<2> The method for producing a polyphenol composition according to <1>, wherein a content of an aqueous medium in the mixture of the hardly water-soluble polyphenol (A) and the water-soluble polyphenol (B) at the heat treatment is preferably 10 mass % or less, more preferably 5 mass % or less, more preferably 2 mass % or less, more preferably 1 mass % or less, even more preferably the mixture does not contain the aqueous medium.

<3> The method for producing a polyphenol composition according to <1> or <2>, wherein a solubility of the water-soluble polyphenol (B) in water at 25° C. is larger than that of the hardly water-soluble polyphenol (A) in water at 2.5° C.

<4> The method for producing a polyphenol composition according to any one of <1> to <3>, wherein the solubility of the hardly water-soluble polyphenol (A) in water at 25° C. is preferably 2 g/L or less, more preferably 1 g/L or less, more preferably 0.5 g/L or less, more preferably 0.2 g/L or less, even more preferably 0.05 q/L or less.

<5> The method for producing a polyphenol composition according to any one of <1> to <4>, wherein the hardly water-soluble polyphenol (A) is preferably one or more selected from the group consisting of flavonols, flavanones, flavones, isoflavones, phenol carboxylic acids, anthocyanidins, hydroxycinnamic acid derivatives, ellagic acid, and lignin, more preferably one or more selected from the group consisting of rutin, quercitrin, isoquercitrin, quercetin, myricitrin, myricetin, kaempferol, hesperidin, neohesperidin, hesperetin, naringin, ringenin, prunin, astragalin, apiin, apigenin, daidzein, daidzin, glycitein, glycitin, genistein, genistin, curcumin, delphinidin, delphin, nasunin, peonidin, peonin, petunin, malvidin, malvin, enin, cyanidin, leukocyanidin, cyanine, chrysanthemine keracyanin, idaein mecocyanin, pelargonidin, callistephin, resveratrol, caffeic acid, ferulic acid, p-coumaric acid, ellagic acid, sesamin, sesaminol, sesamolin, and sesamol, even more preferably one or more selected from the group consisting of hesperidin, ellagic acid, sesamin, and ferulic acid.

<6> The method for producing a polyphenol composition according to any one of <1> to <5>, wherein the solubility of the water-soluble polyphenol (B) in water at 25° C. is preferably 10 g/L or more, more preferably 15 g/L or more, even more preferably 20 g/L or more.

<7> The method for producing a polyphenol composition according to any one of <1> to <6>, wherein the water-soluble polyphenol (B) is preferably one or more selected from the group consisting of sugar adducts of hardly water-soluble polyphenols, methylated products of hardly water-soluble polyphenols, catechins, and chlorogenic acids, more preferably one or more selected from the group consisting of glucosylhesperidin, glucosylrutin, glucosylquercetin, glucosylisoquercitrin, methylhesperidin, methylquercetin, methylresveratrol, methylrutin, catechins, and chlorogenic acids, even more preferably one or more selected from the group consisting of glucosylhesperidin, methylhesperidin, catechins and chlorogenic acids.

<8> The method for producing a polyphenol composition according to any one of <1> to <7>, wherein a mass ratio of the hardly water-soluble polyphenol (A) to the water-soluble polyphenol (B) in the heat treatment step, [(A)/(B)], is preferably 0.05 or more, more preferably 0.09 or more, more preferably 0.1 or more, more preferably 0.11 or more, more preferably 0.13 or more, even more preferably 0.15 or more, and is preferably 2 or less, more preferably 1 or less, more preferably 0.5 or less, more preferably 0.4 or less, even more preferably 0.25 or less, and is preferably from 0.05 to 2, more preferably from 0.09 to 1, more preferably from 0.1 to 0.5, more preferably from 0.11 to 0.4, more preferably from 0.13 to 0.25, even more preferably from 0.05 to 2.

<9> The method for producing a polyphenol composition according to any one of <1> to <8>, wherein a temperature for the heat treatment is preferably equal to or higher than the melting point or glass transition temperature of the polyphenol having the lowest melting point or glass transition temperature among the water-soluble polyphenols (B).

<10> The method for producing a polyphenol composition according to any one of <1> to <9>, wherein the temperature for the heat treatment is higher than the lowest melting point or glass transition temperature of the hardly water-soluble polyphenol (A) or the water-soluble polyphenol (B) preferably by 2° C. or more, more preferably by 5° C. or more, even more preferably by 10° C. or more, and is higher than the lowest melting point or glass transition on temperature of the water-soluble polyphenol (B) preferably by 2° C. or more, more preferably by 5° C. or more, even more preferably by 10° C. or more, and is preferably 200° C. or lower, more preferably 180° C. or lower, and is preferably higher than the lowest melting point or glass transition temperature of the hardly water-soluble polyphenol (A) or the water-soluble polyphenol (B) by 2° C. or more, and up to 180° C., more preferably higher than the lowest melting point or glass transition temperature of the hardly water-soluble polyphenol (A) or the water-soluble polyphenol (B) by 5° C. or more, and up to 130° C., even more preferably higher than the lowest melting point or glass transition temperature of the hardly water-soluble polyphenol (A) or the water-soluble polyphenol (B) by 10° C. or more, and up to 180° C.

<11> The method for producing a polyphenol composition according to any one of <1> to <10>, wherein a cooling temperature of the heat-treated solution is preferably lower than the melting point or glass transition temperature of the polyphenol having the lowest melting point or glass transition temperature of the hardly water-soluble polyphenol (A) and the water-soluble polyphenol (B) and is preferably 100° C. or lower, more preferably 60° C. or lower.

<12> The method for producing a polyphenol composition according to any one of <1> to <11>, wherein a cooling rate from she heat treatment temperature down to 25° C. is preferably 0.2° C./s or more, more preferably 0.5° C./s or more, more preferably 1.0° C./s or more, even more preferably 3.0° C./s or more, and is 100° C./s or less, more preferably 50° C./s or less in the step for cooling the heat-treated solution.

<13> The method for producing a polyphenol composition according to any one of <1> to <12>, further comprising a step for pulverizing the solidified polyphenol composition.

<14> A polyphenol composition obtained by the producing method according to any one of <1> to <13>.

<15> The polyphenol composition according to <14>, wherein an initial solubility of the hardly water-soluble polyphenol (A) in water at 25° C. is preferably from 0.1 to 1000 g/L, more preferably from 0.2 to 100 g/L.

EXAMPLES

[Quantification of the Hardly Water-Soluble Polyphenol]

Quantification of the hardly water-soluble polyphenol was performed using a high performance liquid chromatograph manufactured by Hitachi, Ltd. equipped with a column Cadenza CD-C18 (4.6 mmϕ×150 mm, 3 μm) manufactured by Imtakt Co. at a column temperature of 40° C., in accordance with the gradient method. A mobile phase, solution A, was 0.05 mol/L acetic acid aqueous solution, and the other mobile phase, solution B, was acetonitrile. Flow rate was 1.0 mL/min. Gradient condition was as follows.

| Time (min) | Solution A (%) | Solution B (%) |
|---|---|---|
| 0 | 85 | 15 |
| 20 | 80 | 20 |
| 35 | 10 | 90 |
| 50 | 10 | 90 |
| 50.1 | 85 | 15 |
| 60 | 85 | 15 |

An injection volume of the sample was 10 μL. Ferulic acid was quantified using the absorbance at the wavelength of 320 nm. Hesperidin and sesamin were quantified using the absorbance at the wavelength of 283 nm.

Quantification of ellagic acid was performed using the same apparatus, except that the gradient condition was set as follows.

| Time (min) | Solution A (%) | Solution B (%) |
|---|---|---|
| 0 | 99 | 1 |
| 10 | 90 | 10 |
| 20 | 85 | 15 |
| 40 | 10 | 90 |
| 50 | 10 | 90 |
| 50.1 | 85 | 15 |
| 60 | 85 | 15 |

An injection volume of the sample was 10 μL. Quantification was performed using the absorbance at the wavelength of 254 nm.

[Evaluation of Solubility]

In the case of an ellagic acid composition and a sesamin composition, ellagic acid and sesamin were added to distilled water so as to make the concentration of 1 g/L, respectively. In the case of a ferulic acid composition and a hesperidin composition, ferulic acid and hesperidin were added to distilled water so as to make the concentration of 6 g/L, respectively. The mixtures were shaken for 5 minutes at 25° C. The mixtures were then filtered through a cellulose acetate membrane filter having a pore diameter of 0.2 μm. The filtrates were measured for the concentration of each dissolved component according to the above-mentioned quantification method.

[Measurement of Viscosity]

Viscosity was measured using RE-85 viscometer manufactured by Toki Sangyo Co., Ltd. after making the temperature of the sample to 20° C. The rotor No. 1 was used and the value after revolution for 1 minute at 60 rpm was recorded.

Example 1

Using a spatula, 0.5 g of ellagic acid dihydrate (manufactured by Wako Pure Chemical Industries, Ltd., content of ellagic acid 89 mass %, melting point 300° C. or more, the same shall apply hereafter) and 4.5 g of a methylhesperidin preparation (manufactured by Hamari Chemicals Ltd., content of methylhesperidin 100 mass %, melting point 135° C., the same shall apply hereafter) were mixed, and charged into a twin screw extruder (MiniCTW manufactured by HAAKE). Heating temperature was 140° C. and the screw revolution was 50 rpm. After the mixture was heated for 15 minutes under circulation, the treated solution was discharged. The heat-treated solution was then cooled to 25° C. under the atmosphere at a room temperature, and solidified. The resulting solid was then pulverized using a mill (LM-PLUS manufactured by Iwatani Corporation) for 1 minute to obtain the ellagic acid composition in a powder state. The cooling rate determined from the cooling time from 140° C. to 25° C. was 3.8° C./s. The evaluation results of the heat treatment conditions and the solubility of the composition are shown in Table 1.

Example 2

An ellagic acid composition was obtained by the same treatment as that of Example 1, except that the heating temperature was 160° C. The cooling rate determined from the cooling time from 160° C. to 25° C. was 4.5° C./s. The evaluation results of the heat treatment conditions and the solubility of the composition are shown in Table 1.

Example 3

An ellagic acid composition was obtained by the same treatment as that of Example 1, except that the heating temperature was 180° C. The cooling rate determined from the cooling time from 180° C. to 25° C. was 5.2° C./s. The evaluation results of the heat treatment conditions and the solubility of the composition are shown in Table 1.

Comparative Example 1

An ellagic acid composition was obtained by mixing 0.5 g of ellagic acid dihydrate and 4.5 g of a methylhesperidin preparation with a spatula at 25° C. The evaluation results of the solubility of the composition are shown in Table 1.

Comparative Example 2

An ellagic acid composition was obtained by the same treatment as that of Example 1, except, that the heating temperature was 80° C. The mixture of ellagic acid dihydrate and methylhesperidin was not dissolved during the heat treatment. The evaluation results of the heat treatment conditions and the solubility of the composition are shown in Table 1.

Example 4

Using a spatula, 0.5 g of ellagic acid dihydrate and 4.5 g of a glucosylhesperidin preparation (manufactured by Hayashibara Biochemical Laboratories, Inc., content of glucosylhesperidin 76 mass %, glass transition temperature 150° C.) were mixed, and charged into a test tube. The test tube was immersed in an oil bath and stirred for 5 minutes with a spatula. The temperature of the oil bath was 160° C. The heat-treated solution was cooled to 25° C. under the atmosphere at a room temperature, and solidified. The resulting solid was pulverized in the same manner as that of Example 1 to obtain the ellagic acid composition. The evaluation results of the heat treatment conditions and the solubility of the composition are shown in Table 1.

Example 5

An ellagic acid composition was obtained by the same treatment as that of Example 4, except that 4.5 g of a chlorogenic acid preparation (manufactured by Takasago international Corporation, content of chlorogenic acid 40 mass %, glass transition temperature 140° C.) was used instead of the glucosylhesperidin preparation. The evaluation results of the heat treatment conditions and the solubility of the composition are shown in Table 1.

Example 6

An ellagic acid composition was obtained by the same treatment as that of Example 4, except that 4.5 g of a catechin preparation (manufactured by DMS Nutritional Products Co., content of epigallocatechin gallate 100 mass %, melting point 147° C.) was used instead of the glucosylhesperidin preparation. The evaluation results of the heat treatment conditions and the solubility of the composition are shown in Table 1.

Comparative Example 3

An ellagic acid composition was obtained by the same treatment as that of Example 1, except that 4.5 g of hydroxypropylmethylcellulose (Metolose SE-06, manufactured by Shin-Etsu Chemical Co., Ltd., glass transition temperature 180° C.) was used instead of the methylhesperidin preparation and that the temperature for heat treatment was 200° C. The evaluation results of the heat treatment conditions and the solubility of the composition are shown in Table 1.

TABLE 1

| | Example 1 | Example 2 | Example 3 | Comparative Example 1 | Comparative Example 2 | Example 4 | Example 5 | Example 6 | Comparative Example 3 |
|---|---|---|---|---|---|---|---|---|---|
| Charge | | | | | | | | | |
| Hardly water-soluble polyphenol (A) | Ellagic acid | Ellagic acid | Ellagic acid | Ellagic acid | Ellagic acid | Ellagic acid | Ellagic acid | Ellagic acid | Ellagic acid |
| Water-soluble polyphenol (B) | Methyl-hesperidin | Methyl-hesperidin | Methyl-hesperidin | Methyl-hesperidin | Methyl-hesperidin | Glucosyl-hesperidin | Chlorogenic acid | Catechin | Hydroxypropyl methylcellulose |

TABLE 1-continued

|  |  | Example 1 | Example 2 | Example 3 | Comparative Example 1 | Comparative Example 2 | Example 4 | Example 5 | Example 6 | Comparative Example 3 |
|---|---|---|---|---|---|---|---|---|---|---|
| Solubility of (A) in water (25° C.) | [g/L] | 0.004 | 0.004 | 0.004 | 0.004 | 0.004 | 0.004 | 0.004 | 0.004 | 0.004 |
| Solubility of (B) in water (25° C.) | [g/L] | 300 or more | 300 or more | 300 or more | 300 or more | 300 or more | 300 or more | 40 | 15 | 300 or more |
| Mass ratio (A)/(B) | [—] | 0.10 | 0.10 | 0.10 | 0.10 | 0.10 | 0.13 | 0.25 | 0.10 | 0.10 |
| Treatment conditions |  |  |  |  |  |  |  |  |  |  |
| Heat treatment temperature | [° C.] | 140 | 160 | 180 | 25 | 80 | 160 | 160 | 160 | 200 |
| Heat treatment time | [min] | 15 | 15 | 15 |  | 15 | 5 | 5 | 5 | 15 |
| Evaluation |  |  |  |  |  |  |  |  |  |  |
| Concentration of dissolved (A) when polyphenol composition was used (25° C.) | [g/L] | 0.256 | 0.423 | 0.510 | 0.004 | 0.007 | 0.242 | 0.326 | 0.302 | 0.122 |

Table 1 shows that the polyphenol composition having an enhanced solubility in water has been obtained according to the method of the present invention.

On the other hand, when hydroxypropylmethylcellulose was used, enhancement in the solubility of the hardly water-soluble polyphenol is not satisfactory, and she solubility in water was insufficient.

Example 7

A ferulic acid composition was obtained by the same treatment as that of Example 2, except that 0.5 g of a ferulic acid preparation (manufactured by Tokyo Chemical Industry Co., Ltd., content of ferulic acid 100 mass %, melting point 174° C.) and 4.5 g of a chlorogenic acid preparation were mixed. The evaluation results of the heat treatment conditions and the solubility of the composition are shown in Table 2.

Comparative Example 4

A ferulic acid composition was obtained by mixing 0.5 g of ferulic acid preparation and 4.5 g of a chlorogenic acid preparation with a spatula at 25° C. The evaluation results of the solubility of the composition are shown in Table 2.

Example 8

A sesamin composition was obtained by the same treatment as that of Example 2, except that 0.5 g of sesamin (manufactured by Kadoya Sesame Mills Inc., content of sesamin 100 mass %, melting point 121° C.) and 4.5 g of a methylhesperidin preparation were mixed. The evaluation results of the heat treatment conditions and the solubility of the composition are shown in Table 2.

Comparative Example 5

A sesamin composition was obtained by mixing 0.5 g of sesamin and 4.5 g of a methylhesperidin preparation with a spatula at 25° C. The evaluation results of the solubility of the composition are shown in Table 2.

Example 9

A hesperidin composition was obtained by the same treatment as that of Example 2, except that 0.5 g of a hesperidin preparation (manufactured by Hamari Chemicals Ltd., content of hesperidin 90 mass %, melting point 260° C.) and 4.5 g of a methylhesperidin preparation were mixed. The evaluation results of the heat treatment conditions and the solubility of the composition are shown in Table 2.

Comparative Example 6

A hesperidin composition was obtained by mixing 0.5 g of a hesperidin preparation and 4.5 g of a methylhesperidin preparation with a spatula at 25° C. The evaluation results of the solubility of the composition are shown in Table 2.

TABLE 2

|  |  | Example 7 | Comparative Example 4 | Example 8 | Comparative Example 5 | Example 9 | Comparative Example 6 |
|---|---|---|---|---|---|---|---|
| Charge |  |  |  |  |  |  |  |
| Hardly water-soluble polyphenol (A) |  | Ferulic acid | Ferulic acid | Sesamin | Sesamin | Hesperidin | Hesperidin |
| Water soluble polyphenol (B) |  | Chlorogenic acid | Chlorogenic acid | Methyl-hesperidin | Methyl-hesperidin | Methyl-hesperidin | Methyl-hesperidin |
| Solubility of (A) in water (25° C.) | [g/L] | 0.660 | 0.660 | 0.00014 | 0.00014 | 0.050 | 0.050 |
| Solubility of (B) in water (25° C.) | [g/L] | 40 | 40 | 300 or more | 300 or more | 300 or more | 300 or more |
| Mass ratio (A)/(B) | [—] | 0.28 | 0.28 | 0.11 | 0.11 | 0.10 | 0.10 |

TABLE 2-continued

|  |  | Example 7 | Comparative Example 4 | Example 8 | Comparative Example 5 | Example 9 | Comparative Example 6 |
|---|---|---|---|---|---|---|---|
| Treatment Conditions |  |  |  |  |  |  |  |
| Heat treatment temperature | [° C.] | 160 | 25 | 160 | 25 | 160 | 25 |
| Heat treatment time | [min] | 10 |  | 10 |  | 10 |  |
| Evaluation |  |  |  |  |  |  |  |
| Concentration of dissolved (A) when polyphenol composition was used (25° C.) | [g/L] | 3.230 | 0.720 | 0.303 | 0.001 | 1.285 | 0.072 |

Table 2 shows that the polyphenol composition having an enhanced solubility in water has been obtained according to the method of the present invention.

Test Example 1

A powdered beverage was prepared by mixing 1 g of the ellagic acid composition obtained in the above-mentioned Example 2 or Comparative Example 3 and 2.5 g of powdered juice of grapefruit. To this powder was added 100 g of distilled water and the mixture was shaken for 20 minutes at 25° C. with a rotary shaker at 150 rpm to obtain the beverage. Samples were taken after shaking for 1 minute and at every 5 minutes of shaking, and were filtered through a cellulose acetate membrane filter having a pore diameter of 0.2 μm. The filtrates were measured for the concentration of ellagic acid. The results are shown in Table 3 and FIG. 1.

TABLE 3

| Shaking time [min] | Ellagic acid composition of Example 2 Dissolved ellagic acid [g/L] | Ellagic acid composition of Comparative Example 3 Dissolved ellagic acid [g/L] |
|---|---|---|
| 0 | 0 | 0 |
| 1 | 0.324 | 0.013 |
| 5 | 0.418 | 0.122 |
| 10 | 0.424 | 0.184 |
| 15 | 0.414 | 0.208 |
| 20 | 0.394 | 0.212 |

As is clear from Table 3 and FIG. 1, the ellagic acid composition of Example 2 had a very high initial solubility in water at 25° C.

In addition, the beverage prepared using the ellagic acid composition of Example 2 had a viscosity of 1.22 mPa·s after 20 minutes, and a feeling as the beverage passes down through the throat, and thus it was suitable as a beverage. On the other hand, the beverage prepared using the ellagic acid composition of Comparative Example 3 had a viscosity of 3.98 mPa·s after 20 minutes.

The invention claimed is:

1. A method for producing a polyphenol composition comprising the following steps (1) and (2):
   (1) heating a mixture of a hardly water-soluble polyphenol (A) and a water-soluble polyphenol (B) to the temperature equal to or higher than the lowest melting point or glass transition temperature of the hardly water-soluble polyphenol (A) or the water-soluble polyphenol (B), thereby obtaining a heat-treated solution, wherein a content of aqueous medium in the mixture at the heat treatment is 10 mass % or less and wherein the water-soluble polyphenol (B) has the solubility in water at 25° C. of 10 g/L or more, and
   (2) cooling and solidifying the thus-obtained heat-treated solution.

2. The method for producing a polyphenol composition according to claim 1, wherein the content of aqueous medium in the mixture of the hardly water-soluble polyphenol (A) and the water-soluble polyphenol (B) at the heat treatment is 5 mass % or less.

3. The method for producing a polyphenol composition according to claim 1, wherein the mixture of the hardly water-soluble polyphenol (A) and the water-soluble polyphenol (B) at the heat treatment does not contain the aqueous medium.

4. The method for producing a polyphenol composition according to claim 1, wherein the temperature for the heat treatment is higher than the lowest melting point or glass transition temperature of the hardly water-soluble polyphenol (A) or the water-soluble polyphenol (B) by 2° C. or more, and up to 200° C.

5. The method for producing a polyphenol composition according to claim 1, wherein the temperature for the heat treatment is higher than the lowest melting point or glass transition temperature of the hardly water-soluble polyphenol (A) or the water-soluble polyphenol (B) by 5° C. or more, and up to 180° C.

6. The method for producing a polyphenol composition according to claim 1, wherein a solubility of the water-soluble polyphenol (B) in water at 25° C. is larger than that of the hardly water-soluble polyphenol (A) in water at 25° C.

7. The method for producing a polyphenol composition according to claim 1, wherein the hardly water-soluble polyphenol (A) has the solubility in water at 25° C. of 2 g/L or less.

8. The method for producing a polyphenol composition according to claim 1, wherein the hardly water-soluble polyphenol (A) is one or more selected from the group consisting of hesperidin, ellagic acid, sesamin, and ferulic acid.

9. The method for producing a polyphenol composition according to claim 1, wherein the water-soluble polyphenol (B) is one or more selected from the group consisting of sugar adducts of hardly water-soluble polyphenols, methylated products of hardly water-soluble polyphenols, catechins, and chlorogenic acids.

10. The method for producing a polyphenol composition according to claim 1, wherein the water-soluble polyphenol (B) is one or more selected from the group consisting of glucosylhesperidin, methylhesperidin, catechins and chlorogenic acids.

11. The method for producing a polyphenol composition according to claim 1, wherein a mass ratio of the hardly water-soluble polyphenol (A) to the water-soluble polyphenol (B) in the heat treatment step, [(A)/(B)], is from 0.05 to 2.

12. The method for producing a polyphenol composition according to claim 1, wherein a mass ratio of the hardly water-soluble polyphenol (A) to the water-soluble polyphenol (B) in the heat treatment step, [(A)/(B)], is from 0.09 to 1.

13. The method for producing a polyphenol composition according to claim 1, wherein a cooling temperature of the heat-treated solution is lower than the melting point or glass transition temperature of the polyphenol having the lowest melting point or glass transition temperature of the hardly water-soluble polyphenol (A) and the water-soluble polyphenol (B).

14. The method for producing a polyphenol composition according to claim 1, wherein a cooling rate from the heat treatment temperature to 25° C. is 0.2° C./s or more in the step for cooling the heat-treated solution.

15. The method for producing a polyphenol composition according to claim 1, further comprising a step for pulverizing the solidified polyphenol composition.

16. A method for producing a polyphenol composition comprising the following steps (1) and (2):
    (1) heating a mixture of a hardly water-soluble polyphenol (A) and a water-soluble polyphenol (B) to the temperature equal to or higher than the lowest melting point or glass transition temperature of the hardly water-soluble polyphenol (A) or the water-soluble polyphenol (B), thereby obtaining a heat-treated solution, wherein a mass ratio of the hardly water-soluble polyphenol (A) to the water-soluble polyphenol (B) in the heat treatment step, [(A)/(B)], is from 0.05 to 2 and wherein a content of aqueous medium in the mixture at the heat treatment is 10 mass % or less, and
    (2) cooling and solidifying the thus-obtained heat-treated solution.

17. A method for producing a polyphenol composition comprising the following steps (1) and (2):
    (1) heating a mixture of a hardly water-soluble polyphenol (A) and a water-soluble polyphenol (B) to the temperature equal to or higher than the lowest melting point or glass transition temperature of the hardly water-soluble polyphenol (A) or the water-soluble polyphenol (B), thereby obtaining a heat-treated solution, wherein a content of aqueous medium in the mixture at the heat treatment is 10 mass % or less, and
    (2) cooling, and thereby solidifying, the heat-treated solution from the heat treatment temperature to 25° C., at a cooling rate of 0.2° C./s or more.

* * * * *